United States Patent [19]

Kesling, Jr. et al.

[11] 4,166,913

[45] Sep. 4, 1979

[54] PREPARATION OF UNSATURATED DIESTERS BY THE CATALYTIC OXIDATIVE CARBONYLATION OF DIOLEFINS WITH AN ENOL ETHER AND AN ALCOHOL

[75] Inventors: Haven S. Kesling, Jr., Drexel Hill; Lee R. Zehner, Media, both of Pa.

[73] Assignee: Atlantic Richfield Company, Los Angeles, Calif.

[21] Appl. No.: 814,012

[22] Filed: Jul. 8, 1977

[51] Int. Cl.² .............................................. C07C 69/52
[52] U.S. Cl. ........................................ 560/204; 560/81; 560/193
[58] Field of Search .......................... 560/204, 193, 81

[56] References Cited

U.S. PATENT DOCUMENTS 3,397,226  8/1968  Fenton .................................. 560/204

FOREIGN PATENT DOCUMENTS 50-130714  10/1975  Japan .

Primary Examiner—Jane S. Myers
Attorney, Agent, or Firm—Delbert E. McCaslin

[57] ABSTRACT

A process for the preparation of an unsaturated diester having the formula

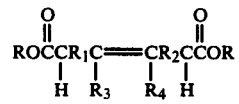

wherein R is an alkyl group of from 1 to 8 carbon atoms or an aralkyl group containing 6 carbon atoms in the ring and from 1 to 4 carbon atoms in the alkyl substituent and $R_1$ to $R_4$ is hydrogen, a halogen, an alkyl group of from 1 to 4 carbon atoms or an aryl group containing 6 carbon atoms in the ring, by reacting carbon monoxide, oxygen, at least a stoichiometric amount of an enol ether or alkoxycycloalkene and at least an equal molar quantity of an alcohol based on the enol ether or alkoxycycloalkene, with a diolefin having the formula

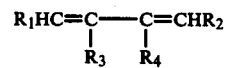

wherein $R_1$, $R_2$, $R_3$ and $R_4$ which may be the same or different is as hereinabove described, in the presence of a catalytic amount of a platinum group metal compound and a copper or iron oxidant salt compound.

Alternatively, a ligand or coordination complex compound of the metal salt compound may be employed as a co-catalyst.

28 Claims, No Drawings

PREPARATION OF UNSATURATED DIESTERS BY THE CATALYTIC OXIDATIVE CARBONYLATION OF DIOLEFINS WITH AN ENOL ETHER AND AN ALCOHOL

BACKGROUND OF THE INVENTION

The oxidative carbonylation of mono-olefins such as ethylene and propylene to prepare carboxylic acids and derivatives employing various catalyst systems, particularly noble metal catalysts is known; see for example, Fenton and Steinwand, Journal of Organic Chemistry, Vol. 37, 2034 (1972) as well as U.S. Pat. Nos. 3,397,226; 3,876,694; 3,907,882; 3,923,883; and 3,960,934.

In an article by Jiro Tsuji, Accounts of Chemical Research, Vol. 2, 144, (1969) and especially bibliographic references (36) and (37) noted therein, the carbonylation of butadiene-isoprene-palladium chloride complexes in alcohol to give 1,4-dichloro-2-butene and ethyl 3-pentenoate and ethyl 5-ethoxy-3-methyl-3-pentenoate and dimethylbutyrolactone, with other minor products is described. In a related article by S. Hosaka and J. Tsuji, Tetrahedron, Vol. 27, 2821–3829 (1971) the palladium catalyzed carbonylation in alcohol of various conjugated dienes and the reaction mechanism are shown.

While oxidative carbonylation reactions are generally known, the prior art does not show or describe the process of the present invention for the oxidative carbonylation of a diolefin, such as butadiene, to prepare an unsaturated diester which may be further processed by catalytic hydrogenation and catalyzed hydrolysis reaction sequences to prepare adipic acid and related derivatives. Hydrogenation of the unsaturated diester produces dialkyl adipates, e.g., dimethyl adipate which may be used as plasticizers and lubricants.

The process of the present invention is directed to the preparation of an unsaturated diester by the catalytic oxidative carbonylation of a diolefin. More particularly, the instant process relates to the synthesis of diesters by reacting carbon monoxide, oxygen, a diolefin such as 1,3-butadiene, isoprene, chloroprene and the like, at least a stoichiometric amount of an enol ether such as methyl vinyl ether or an alkoxycycloalkene such as 1-methoxycyclohexene and at least an equal molar quantity of an alcohol such as methanol based on the enol ether or alkoxycycloalkene, under elevated temperature and pressure conditions in the presence of a catalytic amount of a ruthenium, rhodium, palladium, osmium, iridium or platinum metal salt compound or mixtures thereof, and a copper (I), copper (II), iron (II) or iron (III) oxidant salt compound. Co-catalytic ligands or coordination complex compounds of the metal salt compounds while not required in the process of the invention, may also be employed.

The process of this invention provides an economic process for the preparation of a diester which may be an adipic acid precursor, by the oxidative carbonylation of a conjugated diolefin such as butadiene. There is provided a high conversion of the diolefin employed, especially 1,3-butadiene, and excellent yield selectivity to the diester. Carbonate esters, oxalate esters, carbon dioxide as well as other side reaction products associated with the oxidative carbonylation reaction are obtained in only trace amounts or eliminated by the reaction conditions employed in carrying out the process of the invention. The reaction is catalytic in both the platinum metal salt compound and oxidant salt compound and employs at least stoichiometric quantities of reactant diolefins, carbon monoxide, oxygen and/or air, and enol ether or alkoxycycloalkene as well as an equal molar amount of an alcohol based on the enol ether or alkoxycycloalkene. The reaction can be safely and conveniently carried out under a non-explosive oxygen or air/carbon monoxide atmosphere.

SUMMARY OF THE INVENTION

According to the present invention diolefins are oxidatively carbonylated with carbon monoxide and oxygen or an oxygen-containing gas in the presence of a platinum group metal compound such as a palladium halide, a copper or iron oxidant salt compound such as a copper (II) chloride and at least a stoichiometric amount of an enol ether or alkoxycycloalkene such as methyl vinyl ether and 1-methoxycyclohexene respectively, in addition to at least equal molar quantities of an aliphatic, alicyclic or aralkyl alcohol based on the enol ether or alkoxycycloalkene employed to produce an unsaturated diester. The process is carried out at suitable temperatures and pressures and alternatively contemplates the use of catalytic quantities of various ligands, which will not work in themselves, in conjunction with the platinum group metal salt compound and the oxidant salt.

It is a primary object of this invention to provide a process for the preparation of unsaturated diesters in high yield and high conversion of reactants which diesters may be further processed to adipic acid and adipic derivatives.

It is another object of the invention to provide a novel reaction system for the conversion of carbon monoxide, oxygen, enol ethers or alkoxycycloalkenes, alcohols and diolefins to unsaturated diesters.

It is a further object of this invention to provide a specific catalytic mechanism for the employment of platinum group metal compounds, oxidant salt compounds, enol ethers or alkoxycycloalkenes and alcohols in an oxidative carbonylation process employing a diolefin.

These and other objects and advantages of this invention will become apparent from the description of the invention which follows and from the claims.

DESCRIPTION OF THE INVENTION

In accordance with this invention, an unsaturated diester having the formula

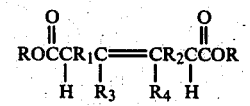

wherein R and $R_1$ to $R_4$ are as hereinafter described, is produced by reacting, under liquid phase conditions, a mixture of carbon monoxide and oxygen or an oxygen-containing gas with a diolefin, an enol ether or alkoxycycloalkene and an alcohol, at elevated temperatures and pressures in the presence of a catalyst system comprising (1) a platinum group metal or platinum group metal compound or mixtures thereof, with or without a ligand or coordination complex compound such as lithium chloride, and (2) a catalytic amount of a copper (I), copper (II), iron (II) or iron (III) metal oxidant salt compound. The enol ether or alkoxycycloalkene employed in at least a stoichiometric quantity based on the diolefin being reacted, performs as a dehydrating agent and is employed in the reaction in conjunction with the alcohol in order to essentially avoid the problems associated with the presence of water in the system which is produced therein by the oxidant-reoxidation reaction. Alkoxycycloalkenes are preferred dehydrating agents. The reactants are initially charged in an essentially anhydrous condition.

A general postulated equation for the reaction of the present invention may for example be represented as follows:

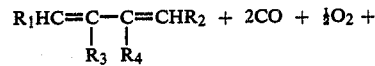
(diolefin)

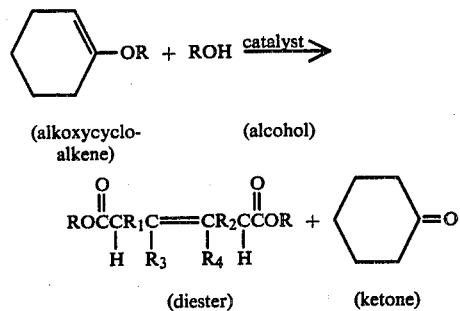

wherein R which preferably are the same, is an alkyl group of from 1 to 8 carbon atoms or an aralkyl group containing 6 carbon atoms in the ring and from 1 to 4 carbon atoms in the alkyl substituent, and $R_1$ to $R_4$ is hydrogen, a halogen, an alkyl group of from 1 to 4 carbon atoms or an aryl group containing 6 carbon atoms in the ring. R may also contain substituents such as amido, alkoxy, amino, carboxy, cyano, fluoro, etc., radicals which in general do not interfere with the reaction of the invention.

The reaction between the diolefin, carbon monoxide, oxygen, alcohol and enol ether or alkoxycycloalkene dehydrating agent may be carried out in an autoclave or any other appropriate reactor. Although the order of addition of reactants and catalyst components may vary, a general procedure is to charge the diolefin, alcohol, dehydrating agent, (preferably an alkoxycycloalkene) platinum group metal compound, oxidant salt compound into the reaction vessel, and if desired a ligand or coordination complex compound, then introduce the proper amount of carbon monoxide and oxygen to the desired reaction pressure and then heat the mixture to the desired temperature for the appropriate period. The reaction can be carried out batchwise or as a continuous process and the order of addition of reactants and catalyst may be varied to suit the particular apparatus employed. The addition of the oxygen or oxygen-containing gas, such as air, can be a pulsed or continuous addition to the reaction system. The reaction products are recovered and treated by any conventional method such as distillation and/or filtration, etc., to effect separation of the diesters from unreacted materials, platinum group metal salt compound, oxidant salt compound, by products, including for example, when reacting 1,3-butadiene, dimethylhex-2,4-diendioate, methylpent-3-enoate, methylpent-2,4-dienoate, methyl-3-methoxypent-4-enoate, methyl-5-methoxypent-3-enoate, dimethyl oxalate and $CO_2$, etc. Catalysts, including solvents which may have been employed, may be recycled to the system.

The diolefins which may be employed in concentrations of from about 10 to 80 weight percent, preferably 20 to 60 weight percent, or on a mole per mole basis with the dehydrating agent employed, and suitable for use in the process of the present invention conform to the general formula

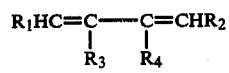

wherein $R_1$ to $R_4$, which may be the same or different, is hydrogen, a halogen, an alkyl group of from 1 to 4 carbon atoms or an aryl group containing 6 carbon atoms in the ring. Representative diolefins within the above noted formula include for example, butadiene, isoprene, chloroprene, 2,3-dimethyl-, 2,3-diethyl-, 2,3-dipropyl- and 2,3-dibutylbutadiene, 1,3- and 2,4-heptadienes, 1,3-pentadiene, piperylene, 2-ethyl-1,3-butadiene, 1-phenylbutadiene, 1,4-diphenylbutadiene, 2-chloro-3-methylbutadiene, 1-chlorobutadiene, 2,5-dimethyl-2,4-hexadiene, 2-bromobutadiene, 2-iodobutadiene, 2-chloro-1-phenylbutadiene, etc. Butadiene and isoprene are the preferred diolefins and butadiene is most preferred.

The enol ethers employed in at least stoichiometric quantities, i.e., at least one mole of enol ether per mole of alcohol employed, and suitable for use in the process of the present invention conform to the general formula

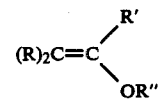

wherein R and R' may be hydrogen or an alkyl group containing from 1 to 8 carbon atoms preferably 1 to 4 carbon atoms. R and R' may also be an alicyclic, aralkyl or an aryl group containing one or more benzenoid rings preferably not more than 3 rings which may be fused or joined by single valency bonds. R" which may be a substituted or unsubstituted alkyl or aralkyl group preferably contain from 1 to 8 carbon atoms in the alkyl chain and from 1 to 2 aryl group substituents when R" is an aralkyl group. Representative enol ethers suitable for use in this invention include for example, methyl vinyl ether, ethyl vinyl ether, n-propyl and isopropyl vinyl ether, n-butyl isobutyl and sec-butyl vinyl ether as well as t-butyl, n-hexyl, n-octyl, 2-ethylhexyl, decyl, cetyl, octadecyl, phenyl and 2,2,2-trifluoroethyl vinyl ether, etc., bis(2-methallyl)vinyl ether, methyl-, ethyl-, propyl-, butyl-1-propenyl ether, etc., 2-buten-2-yl-methyl ether (cis and trans), etc., 2-methyl-2-propen-1-yl methyl ether, etc.

The alkoxycycloalkenes which may be employed in at least stoichiometric quantities, i.e., at least one mole of the alkene per mole of alcohol employed, and suitable for use in the process of the present invention conform to the general formula

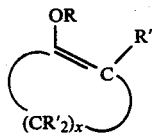

as indicated hereinabove. Representative of such compounds is, for example, 1-methoxy-4-ethylcyclohexene having the structural formula

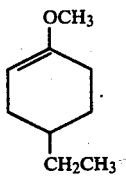

From 5 to 8 carbon atoms may be in the cyclic ring. R may be an alkyl group containing from 1 to 8 carbon atoms preferably 1 to 4 carbon atoms. R may also be an aralkyl group containing one or more benzenoid rings preferably not more than 2 rings which may be fused or joined by single valency bonds. R' may be hydrogen or a straight or branched chain alkyl group containing from 1 to 8 carbon atoms preferably from 1 to 4 carbon atoms in the alkyl chain. x is an integer of from 3 to 6 thus forming a cyclic ring which may have from 5 to 8 carbon atoms.

Representative alkoxycycloalkenes suitable for use in this invention include for example, 1-methoxy-, 1-ethoxy-, 1-propoxy-, 1-butoxy-, 1-isobutoxy-, etc. cyclohexenes, cycloheptenes, cyclopentenes, cyclooctenes, etc., 1-methoxy-4-methylcyclohexene, 1-methoxy-2-methyl-4-ethylcyclohexene, 1-ethoxy-4-butylcycloheptene, 1-methoxy-2-methyl-6-ethylcyclooctene, etc.

The alcohols which are employed in at least equal molar quantities based on the enol ethers or alkoxycycloalkenes and suitable for use in the process of the present invention can be monohydric saturated aliphatic and alicyclic alcohols or aralkyl alcohols and may contain other substituents such as amido, alkoxy, amino, carboxy, cyano, etc., radicals in addition to the hydroxyl group. The substituents, in general, do not interfere with the reaction of the invention.

The alcohols which are employed in at least molar quantities equal to the molar quantity of enol ether or alkoxycycloalkene employed may be primary, secondary or tertiary alcohols and conform to the general formula ROH, wherein R is an optionally substituted aliphatic or alicyclic group preferably containing from 1 to 8 carbon atoms. R may also be a substituted or unsubstituted aralkyl group. Representative alcohols especially suitable for use in this invention are saturated monohydric alcohols such as methyl, ethyl, n-, iso, sec-, and tert-butyl, amyl, hexyl, octyl, n- and isopropyl, benzyl, chlorobenzyl and methoxybenzyl alcohols as well as, for example, tolylcarbinol, cyclohexanol, heptanols, 2-ethyl hexanol, and methyl cyclohexanol, alcohols, and the like. The preferred alcohols are the primary and secondary monohydric saturated lower aliphatic alcohols, such as methanol, ethanol, 1- and 2-propanol, n-butyl alcohol, etc., containing up to 4 carbon atoms. The R group of the alcohol may be different from the R' or R" of the enol ether or alkoxycycloalkene dehydrating agents noted hereinabove, resulting in the preparation of mixed diesters.

The platinum group metal compounds which may be employed in the process of this invention as catalyst are the palladium, platinum, rhodium, ruthenium, iridium, and osmium salts or mixtures thereof. Among the chemical forms of the platinum group metal salt compounds which can be used as such or as mixtures or formed in the reaction system from the metals per se are for example the palladium, platinum, rhodium, ruthenium, iridium and osmium, halides, sulfates, nitrates, oxides, oxalates, acetates and trifluoroacetates, preferably the palladium (II) halides, particularly palladium (II) chloride. Representative catalytic platinum group metal salt compounds include, for example palladium (II) chloride, platinum (II) chloride, rhodium (III) chloride, ruthenium (III) chloride, palladium (II) sulfate, palladium (II) acetate, palladium (II) trifluoroacetate, palladium (II) iodide, rhodium (III) bromide, iridium (III) chloride, platinum (II) sulfate, osmium (II) chloride, palladium (II) oxide, osmium tetroxide, iridium (III) sulfate, etc. As indicated above the metals as such may be added to the reaction as part of the catalyst mixture, the salt compound being formed in situ from at least a portion of the platinum group metal under reaction conditions.

The palladium, platinum, rhodium, ruthenium, osmium and iridium compounds employed may be in a homogeneous state in the reaction mixture at reaction conditions. Thus, the compounds may be present in solution, or suspension and may also be on support materials such as alumina, silica gel, aluminosilicates, activated carbon or zeolites or may be anchored to a polymer support. The compounds may be partially or completely soluble under reaction conditions. The reaction is generally carried out in the presence of a catalytic proportion of the platinum group metal salt compound and will proceed with small amounts of the metal salt compounds hereinabove described. Generally the proportions of the platinum group metal salt compound used in the reaction will be equivalent to between about 0.001 to 5 weight percent of the diolefin employed and are preferably employed in amounts between about 0.01 to 2 percent by weight of the diolefin employed. Larger or smaller amounts may be employed at varied pressures and temperatures.

As mentioned hereinabove, alternatively, a ligand or coordination complex compound of the platinum group metal salt compound may be employed in the process of the invention as co-catalyst in the catalytic mixture and thereby also achieve a pronounced increase in the selectivity for the unsaturated diester. The ligands may be, for example, alkyl or aryl phosphines, arsines, or stibines or salts of the alkali metals, e.g., lithium, sodium, potassium, rubidium, cesium salts, such as lithium iodide, sodium chloride, potassium bromide, lithium acetate, lithium chloride, etc. The complexes of the metal salt compounds which are suitable for use in the process of the present invention include complex compounds of palladium, platinum, rhodium, ruthenium, osmium and iridium. The complex compounds may contain one or more atoms of the salt metals in the molecule and when more than one such atom is present, the metals may be the same or different. The mono- or polydentate ligands which are present in the molecule of the complex compounds and in which at least one of the electron-donating atoms is an atom of phosphorous, arsenic or antimony or a halide ion containing a lone pair of electrons may be, for example, organo-phosphines, -arsines and -stibines. Suitable mono-dentate ligands include alkyl phosphines such as trimethylphosphine and tributylphosphine, arylphosphines such as diethylphenylphosphine and radicals derived from such phosphines, for example the radical having the formula—P(CH$_3$)$_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is preferred to employ the alkali metal halides, particularly the lithium halides such as lithium chloride and lithium iodide.

Benzonitrile, acetonitrile, isocyanates, isothiocyanates, pyridine, pyridyls, pyrimidine, quinoline, isoquinoline may also serve as suitable ligands to modify the platinum group metal catalyst activity or catalyst solubility.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen, and halogen atoms; groups which may be bonded to the metal include, for example hydrocarbyl, hydrocarbyloxy, carbonyl, nitrosyl, cyano and SnCl$_3$ groups; molecules which may be bonded to the metal include, for example organic isocyanides and isothiocyanates. Examples of suitable complex compounds are those represented by the following formulae:

RhBr$_3$(PPhEt$_2$)$_3$
RhCl(CO)(PPhEt$_2$)$_2$
Rh(Ph$_2$PCH$_2$CH$_2$PPh$_2$)$_2$Cl
Rh[(PhO)$_3$P]$_3$Cl
Li$_2$PdI$_4$
Rh(CO)Cl(AsEt$_3$)$_2$
RhCl(CO)(PEt$_3$)$_2$
PdCl$_2$(PPh$_3$)$_2$
PdI$_2$(PPh$_3$)$_2$
PtCl$_2$(p-ClC$_6$H$_4$PBu$_2$)$_2$
(PhCN)$_2$PdCl$_2$

The complex compounds employed may be introduced into the reaction mixture as such, or they may be formed in situ from a suitable platinum group metal or metal compound noted above and the desired ligand.

The ligand or complex compounds may be used in catalytic amounts of from 0 to 3 percent preferably from 0.1 to 1 percent by weight of the diolefin to be reacted although larger or smaller amounts may be employed at varied pressures or reaction rates.

The oxidant salt compounds which may be employed in an essentially anhydrous condition in the process of the present invention and in catalytic amounts of from 0.1 to 10 weight percent preferably 0.50 to 6 weight percent include the iron (II), iron (III), copper (I) and copper (II) salts such as the halides, sulfates, trifluoroacetates, nitrates, oxalates, naphthenates, hex-3-endioates or acetates and preferably copper (II) chloride and iron (II) chloride. Representative oxidant salts include, for example, copper (II) sulfate, copper (II) trifluroacetate, copper (II) acetate, copper (II) oxalate, copper (II) triflate, copper (II) fluorosulfonate, copper (I) chloride, copper (I) sulfate, iron (III) sulfate, iron (II) iodide, iron (II) chloride, iron (III) acetate, iron (III) oxalate, copper (II) hex-3-endioate, iron (II) hex-3-endioate and iron (III) trifluoroacetate.

While not necessary to the reaction of the present invention, it is often desirable to add a small amount of an acid to aid in initiating the reoxidation (by oxygen) of copper (I) to copper (II) or iron (II) to iron (III). Suitable acids include for example hydrochloric, hydrobromic, sulfuric, phosphoric and acetic in concentrations of from 0–2 weight percent of diolefin.

Solvents, if desired, which are chemically inert to the components of the reaction system may be employed, and in some cases, especially in the oxidative carbonylation of 1,3-butadiene, will improve the selectivity and conversion to the desired C$_6$-unsaturated diester as well as the catalyst solubility or boiling point range for product and catalyst recovery. Suitable solvents include for example, dioxane, dimethylcarbonate, dimethyladipate, benzene, nitrobenzene, acetonitrile, tetrahydrofuran, methyl acetate, ethyl acetate, isopropyl acetate, n-propyl formate, butyl acetates, cyclohexyl acetate, n-propyl benzoate, lower alkyl phthalates, etc., the alkyl sulfones and sulfoxides such as propyl ethyl sulfoxide, diisopropyl sulfone, diisooctyl sulfoxide, acetone, cyclohexanone, methyl formate, etc.

The process of the present invention can be suitably performed by introducing the oxygen and carbon monoxide at a desired pressure into contact with the diolefin, alcohol, dehydrating agent, the platinum group metal salt compound and the copper or iron oxidant salt and possibly a co-catalytic amount of a ligand or coordination complex and heating to the desired temperature. In general, a carbon monoxide pressure of about 15 psig to about 5000 psig partial pressure and preferably from 500 psig to about 1800 psig is employed. Stoichiometric quantities of carbon monoxide are generally employed. However, an excess of carbon monoxide may be employed, for example, in continuous processes where a large excess of or high carbon monoxide requirements are generally utilized, a suitable recycle of the unreacted carbon monoxide may be employed. The reaction will proceed at temperatures of from about 25° C. to 200° C. It is generally preferred to operate the process at temperatures in the range of 80° C. to 150° C. to obtain a convenient rate of reaction with the particular diolefin. Lower temperature may be employed but the reaction rate is slower. Higher temperatures may also be used depending on the diolefin to be reacted. At the higher temperatures the diolefin employed may be in the vapor state. Heating and/or cooling means may be employed interior and/or exterior of the reaction to maintain the temperature within the desired range.

At least stoichiometric amounts of oxygen or an oxygen-containing gas such as air may be employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent. Oxygen itself may be diluted with an inert gas such as nitrogen, carbon dioxide or helium.

The reaction time is generally dependent upon the diolefin being reacted, temperature, pressure and on the amount and type of the catalyst, oxidant, alcohol and dehydrating agent being charged as well as the type of equipment being employed. Reaction times will vary dependent on whether the process is continuous or batch and may vary from 10 to 600 minutes. Reaction time for butadiene is generally about 120 minutes.

The following examples are provided to illustrate the invention in accordance with the principles of this invention but are not to be construed as limiting the invention in any way except as indicated by the appended claims.

Although the process of the present invention will primarily be directed to the oxidative carbonylation of 1,3-butadiene to produce the unsaturated diester dimethyl-hex-3-endioate, along with dimethyl hex-2,4-diendioate, important precursors for the preparation of adipic acid, it is not intended that the process be limited to the butadiene type diolefins and those skilled in the art will recognize that the present invention is broadly applicable to the oxidative carbonylation of other conjugated diolefins, within the formula as hereinabove set forth, to produce other diester products such as a 1,3-pentadiene to dimethyl-2-methylhex-3-endioate, 2,5-dimethyl-2,4-hexadiene to dimethyl-2,2,5,5-tetramethylhex-3-endioate and 1,4-diphenylbutadiene to dimethyl-2,5-diphenylhex-3-endioate.

In the examples which follow the reactions were carried out in a 500 ml. nickel-molybdenum (HASTELLOY alloy) stirred autoclave or 500 ml. titanium lined stirred autoclave. The liquid feed and solid catalyst components were charged into the autoclave as homogeneous solutions where possible. The diolefins were charged into a sight glass and allowed to come to thermal equilibrium before being charged into the autoclave as a liquid under pressure. Carbon monoxide was charged into the autoclave to the desired pressure followed by heating to the desired reaction temperature. Total system pressure was adjusted to the desired level by the addition of more carbon monoxide. Oxygen or air was added and a non-explosive carbon monoxide/oxygen gas mixture maintained. Where oxygen was employed, carbon monoxide was pulsed into the autoclave to sweep the oxygen out of the pressure tubing. Cooling water was circulated through the internal autoclave cooling coils to maintain the desired reaction temperature and to control the reaction exotherm observed upon the addition of reactant oxygen. After each gas uptake levelled out, total system pressure was readjusted and additional oxygen added. The procedure of charging oxygen of air increments and sweeping out the pressure lines with CO was repeated until no more gas uptake was observed or for the desired reaction time.

Upon completion of the reaction, the reactor was cooled to ambient temperature and vented to ambient pressure and gas samples obtained. Solids were separated from liquids by vacuum filtration. The gaseous product volume was measured and analyzed by mass spectral analysis (MS) and the liquid product was analyzed by gas-liquid chromatography (glc).

Diolefin conversions were calculated on the basis of moles of diolefin consumed by the reaction. Product selectivities were based on the millimoles of diolefin required to make the diester and by-products or on the mmoles of carbon monoxide consumed in preparing the diester and by-products. The amount of unreacted diolefin was obtained by MS analysis of the gases and glc analysis for diolefin in the liquid product.

EXAMPLES 1 to 4

In Examples 1 to 4 a solution of an alcohol and a dehydrating agent was charged into the autoclave along with 0.444 g. (2.5 mmole) palladium (II) chloride, 3.36 g. (25 mmole) copper (II) chloride and 0.21 g. (5 mmole) lithium chloride. 1,3-butadiene was charged into the autoclave as a liquid under pressure. The reaction temperature was 100° C. and the total initial carbon monoxide pressure was 1600 psig. The reaction was initiated by a 100 psig charge of oxygen and 100 psig line purging charge of carbon monoxide giving a total system pressure of 1800 psig. A strong exotherm and pressure drop of 150–200 psig over a course of 20 minutes was observed. The oxygen cycle was repeated five more times in increments of 50 psig oxygen and 100 psig carbon monoxide at intervals of 20 minutes during an autoclave residence time of 120 minutes. A total pressure drop of about 1000 psig was observed. The reaction was terminated before completion and the autoclave cooled to ambient temperature and vented to ambient pressure. The alcohol, dehydrating agent and amount of 1,3-butadiene employed and analytical results giving the conversion and selectivities to product dimethylhex-3-endioate is shown in Table 1. An average yield of 36 percent diester was obtained in Examples 1 to 4.

TABLE 1

| Ex. | 1,3-butadiene Charged g. (mmoles) | Alcohol (mmole) | Dehydration[1] Agent (mmole) | 1,3-Butadiene Conversion (%) | Diester Selectivity Based on 1,3-Butadiene | Diester Selectivity Based on CO |
|---|---|---|---|---|---|---|
| 1 | 27 g. (500) | CH$_3$OH (500) | MOC (500) | 52 | 86 mole % | 73 mole % |
| 2 | 27 g. (500) | C$_2$H$_5$OH (500) | EOC (500) | 48 | 85 mole % | 75 mole % |
| 3 | 27 g. (500) | C$_4$H$_9$OH (500) | BOC (500) | 50 | 83 mole % | 78 mole % |
| 4 | 54 g. (1000) | CH$_3$OH (1000) | MOC (1000) | 37 | 82 mole % | 79 mole % |

[1] MOC - 1-methoxycyclohexene
EOC - 1-ethoxycyclohexene
BOC - 1-butoxycyclohexene

EXAMPLES 5 to 33

In Examples 5 to 33 which follow in table form the procedure and general operating conditions of Examples 1 to 4, except as specifically noted, was repeated employing 1 mole of diolefin, 1 mole of dehydrating agent, 1 mole of alcohol, 5.0 millimole of platinum group metal compound catalyst, oxidant salt compound and with or without a ligand compound. Gaseous and liquid products were analyzed by mass spectral analysis (MS) and gas-liquid chromatography (glc) respectively.

The reaction conditions, reactants, catalysts and oxidants employed in Examples 5 to 33 are set forth in Table 2 with the results showing the main product yield, percent diolefin conversion and mole percent selectivities based on the diolefin summarized in Table 3.

TABLE 2

| Ex. | °C. Temp. | (psig) Pressure | Time Mins. | (1 mole) Diolefin | Alcohol (mmole) | Dehydration Agent | (5.0 mm) Catalyst | Oxidant (mmole) | Ligand (mmole) |
|---|---|---|---|---|---|---|---|---|---|
| 5 | 100 | 1800 | 120 | BD[(1)] | MeOH[(2)] (1000) | MOC[(3)] | $PdCl_2$ | $CuCl_2$ (12.5) | LiCl (10.0) |
| 6 | 100 | 1800 | 120 | BD | MeOH (1000) | MOP[(4)] | $PdCl_2$ | $CuCl_2$ (12.5) | LiCl 10.0 |
| 7 | 110 | 1800 | 125 | BD | MeOH (1000) | MOC | $PdCl_2$ | $FeCl_2$ (25.0) | LiCl (10.0) |
| 8 | 120 | 1800 | 130 | BD | MeOH (1000) | MOC | $PdBr_2$ | $CuBr_2$ (12.5) | LiBr (10.0) |
| 9 | 100 | 1800 | 120 | BD | MeOH (1000) | MOP | $PdBr_2$ | $CuBr_2$ (12.5) | LiBr (10.0) |
| 10 | 125 | 450 | 120 | IP[(5)] | MeOH (1000) | MOC | $PdCl_2$ | $CuCl_2$ (25.0) | LiCl (10.0) |
| 11 | 100 | 1800 | 120 | IP | MeOH (1000) | MOC | $PdCl_2$ | $FeCl_2$ (25.0) | LiCl (10.0) |
| 12 | 125 | 3000 | 120 | IP | MeOH (1000) | MOC | $PdCl_2$ | $FeCl_2$ (25.0) | LiCl (10.0) |
| 13 | 125 | 1000 | 120 | CP[(6)] | MeOH (1000) | MOP | $PdCl_2$ | $CuCl_2$ (25.0) | LiCl (10.0) |
| 14 | 100 | 1800 | 120 | CP | MeOH (1000) | MOC | $PdI_2$ | $Cu(OAc)_2$[(17)] (25.0) | LiI (10.0) |
| 15 | 135 | 3000 | 120 | CP | MeOH (1000) | MOC | $PdBr_2$ | $CuBr_2$ (25.0) | LiI (10.0) |
| 16 | 125 | 1800 | 360 | DPBD[(7)] | MeOH (1000) | MOC | $RuCl_3$ | $CuCl_2$ (25.0) | LiCl (10.0) |
| 17 | 150 | 1800 | 180 | DPBD | MeOH (1000) | MOC | $PdCl_2$ | $Cu_2Cl_2$ (12.5) | — |
| 18 | 125 | 3000 | 120 | DPBD | MeOH (1000) | MOC | $PdBr_2$ | $CuBr_2$ (25.0) | LiBr (10.0) |
| 19 | 125 | 3000 | 120 | BD | MeOH (1000) | MOC | $PtCl_4$ | $CuCl_2$ (25.0) | LiCl (10.0) |
| 20 | 125 | 3000 | 120 | BD | MeOH (1000) | MOC | $RhCl_3$ | $CuCl_2$ (25.0) | LiCl (10.0) |
| 21 | 100 | 1800 | 120 | BD | MeOH (1000) | MOC | $Na_2PdCl_4$ | $CuCl_2$ (25.0) | — |
| 22 | 100 | 1800 | 120 | BD | MeOH (1000) | MOC | $K_2PdCl_4$ | $CuCl_2$ (25.0) | — |
| 23 | 125 | 250 | 120 | BD | MeOH (1000) | MOC | $Pd(\phi CN)_2Cl_2$[(8)] | $CuCl_2$ (25.0) | — |
| 24 | 100 | 1800 | 120 | BD | MeOH (1000) | MVE[(9)] | $PdCl_2$ | $CuCl_2$ (25.0) | KCl (10.0) |
| 25 | 100 | 3000 | 120 | BD | MeOH (1000) | MOC | $PdCl_2$ | $FeCl_2$ (25.0) | LiCl (10.0) |
| 26 | 100 | 3000 | 120 | BD | MeOH (1000) | MOC | $PdCl_2$ | $FeCl_3$ (25.0) | LiCl (10.0) |
| 27 | 100 | 1800 | 120 | BD | MeOH (1000) | MOC | $PdBr_2$ | $Cu_2Br_2$ (25.0) | KBr (10.0) |
| 28 | 75 | 1800 | 120 | BD | MeOH (1000) | MOC | $PdI_2$ | CuI (25.0) | LiI (10.0) |
| 29 | 125 | 3000 | 180 | BD | MeOH (1000) | MOC | Pd(metal) | $Cu_2Cl_2$ (25.0) | LiCl (10.0) |
| 30 | 100 | 3000 | 120 | BD | EtOH[(10)] (1000) | EOC[(11)] | $PdCl_2$ | $CuCl_2$ (25.0) | LiCl (10.0) |
| 31 | 100 | 3000 | 120 | BD | PrOH[(12)] (1000) | POC[(13)] | $PdCl_2$ | $CuCl_2$ (25.0) | LiCl (10.0) |
| 32 | 100 | 3000 | 180 | BD | BuOH[(14)] (1000) | BOC[(15)] | $PdCl_2$ | $CuCl_2$ (25.0) | NaCl (10.0) |
| 33 | 100 | 3000 | 120 | BD | EtOH (1000) | EVE[(16)] | $PdCl_2$ | $CuCl_2$ (25.0) | LiCl (10.0) |

Key
[(1)] BD - 1,3-butadiene
[(2)] MeOH - methanol
[(3)] MOC - 1-methoxycyclohexene
[(4)] MOP - 2-methoxypropene
[(5)] IP - Isoprene
[(6)] L CP - chloroprene
[(7)] DPBD - 1,4-diphenylbutadiene
[(8)] $Pd(\phi CN)_2Cl_2$ - dichloro-bis(benzo-nitrile)palladium (II)
[(9)] MVE - methyl vinyl ether
[(10)] EtOH - ethyl alcohol
[(11)] EOC - 1-ethoxycyclohexene
[(12)] PrOH - propyl alcohol
[(13)] POC - 1-propoxycyclohexene
[(14)] BuOH - butyl alcohol
[(15)] BOC - 1-butoxycyclohexene
[(16)] EVE - ethyl vinyl ether
[(17)] $Cu(OAc)_2$ - copper acetate

TABLE 3

| Ex. | Product (g./mmoles) | % Conversion | Mole % Diester Selectivity based on 1,3-butadiene | Mole % Diester Selectivity based on CO |
|---|---|---|---|---|
| 5 | dimethylhex-3-endioate (36.12/210.0) | 43 | 84 | 74 |
| 6 | dimethylhex-3-endioate (24.30/141.3) | 30 | 81 | 73 |
| 7 | dimethylhex-3-endioate (24.90/144.8) | 30 | 83 | 73 |
| 8 | dimethylhex-3-endioate (36.12/210.0) | 43 | 84 | 73 |
| 9 | dimethylhex-3-endioate (27.88/162.1) | 35 | 82 | 75 |
| 10 | dimethyl-3-methylhex-3-endioate (30.08/161.7) | 21 | 77 | 69 |
| 11 | dimethyl-3-methylhex-3-endioate (44.77/240.7) | 29 | 83 | 76 |
| 12 | dimethyl-3-methylhex-3-endioate (59.18/318.2) | 37 | 86 | 81 |
| 13 | dimethyl-3-chlorohex-3-endioate (33.7/163.3) | 23 | 71 | 67 |
| 14 | dimethyl-3-chlorohex-3-endioate (45.10/218.4) | 28 | 78 | 71 |
| 15 | dimethyl-3-chlorohex-3-endioate (55.20/267.3) | 33 | 81 | 78 |
| 16 | dimethyl-2,5-diphenylhex-3-endioate (70.76/218.4) | 28 | 78 | 69 |
| 17 | dimethyl-2,5-diphenylhex-3-endioate (36.45/112.5) | 15 | 75 | 64 |
| 18 | dimethyl-2,5-diphenylhex-3-endioate (51.19/158.0) | 20 | 79 | 73 |
| 19 | dimethylhex-3-endioate (44.58/259.2) | 32 | 81 | 76 |
| 20 | dimethylhex-3-endioate (48.54/282.2) | 34 | 83 | 72 |
| 21 | dimethylhex-3-endioate (52.63/306.0) | 36 | 85 | 80 |
| 22 | dimethylhex-3-endioate (54.90/319.2) | 38 | 84 | 78 |
| 23 | dimethylhex-3-endioate (23.48/136.5) | 35 | 39 | 87 |
| 24 | dimethylhex-3-endioate (42.66/248.0) | 31 | 80 | 72 |
| 25 | dimethylhex-3-endioate (40.76/237.0) | 30 | 79 | 74 |
| 26 | dimethylhex-3-endioate (37.56/218.4) | 28 | 78 | 71 |
| 27 | dimethylhex-3-endioate (46.68/277.2) | 33 | 84 | 72 |
| 28 | dimethylhex-3-endioate (52.82/307.1) | 37 | 83 | 77 |
| 29 | dimethylhex-3-endioate (44.58/259.2) | 32 | 81 | 73 |
| 30 | diethylhex-3-endioate (62.16/310.8) | 37 | 84 | 79 |
| 31 | dipropylhex-3-endioate (60.94/267.3) | 33 | 81 | 73 |
| 32 | dibutylhex-3-endioate (62.98/246.0) | 30 | 82 | 69 |
| 33 | diethylhex-3-endioate (61.20/306.0) | 36 | 85 | 77 |

We claim:

1. A process for the preparation of an unsaturated diester having the formula

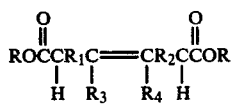

wherein R is an alkyl group of from 1 to 8 carbon atoms or an aralkyl group containing 6 carbon atoms in the ring and from 1 to 4 carbon atoms in the alkyl substituent and $R_1$, $R_2$, $R_3$ and $R_4$ is hydrogen, a halogen, an alkyl group of from 1 to 4 carbon atoms or an aryl group containing 6 carbon atoms in the ring, which comprises reacting a diolefin having the formula

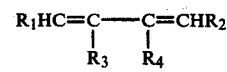

wherein $R_1$, $R_2$, $R_3$ and $R_4$ which may be the same or different are as above described, with a mixture of carbon monoxide and oxygen and at least a stoichiometric amount of an enol ether or alkoxycycloalkene and an equal molar quantity of a monohydric saturated aliphatic, alicyclic or aralkyl alcohol based on the enol ether or alkoxycycloalkene at a pressure of between about 15 psig and 5000 psig and at a temperature in the range of about 25° C. to 200° C. in the presence of an effective amount of a catalytic mixture of a platinum group metal compound or mixtures thereof and a copper (I), copper (II), iron (II) or iron (III) oxidant salt compound and recovering the desired unsaturated diester.

2. A process according to claim 1 wherein the diolefin is selected from the group consisting of 1,3-butadiene, isoprene, chloroprene, and 1,4-diphenylbutadiene.

3. A process according to claim 2 wherein the diolefin is 1,3-butadiene.

4. A process according to claim 1 wherein the enol ether is selected from methyl vinyl ether, ethyl vinyl ether or 2-methoxypropene.

5. A process according to claim 1 wherein the alkoxycycloalkene is selected from the group consisting of 1-methoxycyclohexane, 1-ethoxycyclohexene, 1-propoxycyclohexene or 1-butoxycyclohexene.

6. A process according to claim 5 wherein the alkoxycycloalkene is 1-methoxycyclohexane.

7. A process according to claim 1 wherein the monohydric saturated aliphatic, alicyclic or aralkyl alcohol contains from 1 to 20 carbon atoms and may contain other substituents which would not interfere with the reaction.

8. A process according to claim 7 wherein the alcohol is an unsubstituted aliphatic alcohol containing from 1 to 8 carbon atoms.

9. A process according to claim 8 wherein the alcohol is methyl alcohol, ethyl alcohol, propyl alcohol or butyl alcohol.

10. A process according to claim 9 wherein the alcohol is methyl alcohol.

11. A process according to claim 1 wherein the pressure is between about 500 psig and 1800 psig.

12. A process according to claim 1 wherein the temperature is in the range of from about 80° C. to 150° C.

13. A process according to claim 1 wherein the platinum group metal compound is selected from the group consisting of palladium, ruthenium, rhodium, and platinum, halides, cyanates, sulfates, nitrates, oxides, oxalates, acetates, and trifluoroacetates or mixtures thereof.

14. A process according to claim 13 wherein the platinum group metal compound is selected from palladium (II) chloride, palladium (II) bromide, palladium (II) iodide, rhodium (III) chloride, ruthenium (III) chloride or platinum (II) chloride.

15. A process according to claim 14 wherein the platinum group metal compound is palladium (II) chloride.

16. A process according to claim 14 wherein the platinum group metal compound is palladium (II) bromide.

17. A process according to claim 1 wherein the oxidant salt compound is selected from the group consisting of copper (I), copper (II), iron (II) and iron (III) halides, sulfates, trifluoroacetates, oxalates, naphthenates, nitrates and acetates.

18. A process according to claim 17 wherein the oxidant salt compound is selected from the group consisting of copper (II) chloride, copper (II) bromide, copper (II) iodide, iron (II) chloride, iron (III) chloride and copper (II) acetate.

19. A process according to claim 18 wherein the oxidant salt compound is copper (II) chloride.

20. A process according to claim 18 wherein the oxidant salt compound is copper (II) bromide.

21. A process according to claim 18 wherein the oxidant salt compound is iron (III) chloride.

22. A process according to claim 1 wherein the reaction is carried out in the presence of an organic mono- or poly-dentate ligand or coordination complex compound selected from the group consisting of alkyl, aryl and halogen substituted phosphines, arsines, stibines, and alkali metal salts.

23. A process according to claim 22 wherein the ligand or coordination complex is lithium chloride.

24. A process according to claim 22 wherein the ligand or coordination complex is lithium bromide.

25. A process according to claim 22 wherein the ligand or coordination complex is potassium chloride, potassium bromide, or sodium chloride.

26. A process for the preparation of dimethylhex-3-endioate which comprises reacting 1,3-butadiene with a mixture of carbon monoxide and oxygen, at least a stoichiometric quantity of 1-methoxycyclohexene and an equal molar quantity of methyl alcohol based on the 1-methoxycyclohexene, at a pressure of between about 500 psig and 1800 psig and at a temperature in the range of from about 80° C. to 150° C. in the presence of an effective amount of a palladium metal salt compound and a copper (II) oxidant salt compound.

27. A process according to claim 26 wherein the palladium metal salt compound is palladium (II) chloride, and the copper (II) oxidant salt compound is copper (II) chloride.

28. A process according to claim 27 wherein the reaction is carried out in the presence of a catalytic amount of lithium chloride.

* * * * *